United States Patent
Jikuhara et al.

(10) Patent No.: US 12,288,612 B2
(45) Date of Patent: Apr. 29, 2025

(54) INFORMATION PROCESSING APPARATUS, METHOD, AND NON-TRANSITORY COMPUTER READABLE MEDIUM

(71) Applicant: TOYOTA JIDOSHA KABUSHIKI KAISHA, Toyota (JP)

(72) Inventors: Yoshikazu Jikuhara, Miyoshi (JP); Seii Sai, Yokohama (JP); Ibuki Shimada, Miyoshi (JP); Takahiro Aoki, Saitama (JP); Keishi Kinoshita, Tokyo-to (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 153 days.

(21) Appl. No.: 18/312,056

(22) Filed: May 4, 2023

(65) Prior Publication Data

US 2023/0360785 A1    Nov. 9, 2023

(30) Foreign Application Priority Data

May 6, 2022    (JP) ................................. 2022-076659

(51) Int. Cl.
*G16H 40/20*    (2018.01)
*G06Q 30/0208*    (2023.01)

(52) U.S. Cl.
CPC ......... *G16H 40/20* (2018.01); *G06Q 30/0208* (2013.01); *G06Q 2240/00* (2013.01)

(58) Field of Classification Search
CPC . G16H 40/20; G06Q 30/0208; G06Q 2240/00
See application file for complete search history.

(56) References Cited

U.S. PATENT DOCUMENTS

| 2019/0122760 A1* | 4/2019 | Wang .................... G16H 10/60 |
| 2020/0265345 A1 | 8/2020 | Ishiwata et al. |
| 2021/0035038 A1* | 2/2021 | Suzuki ............. G06Q 10/06311 |

FOREIGN PATENT DOCUMENTS

| JP | 10105611 A * | 4/1998 |
| JP | 2019075047 A | 5/2019 |
| JP | 2020135121 A | 8/2020 |
| JP | 2021022332 A | 2/2021 |
| JP | 2021086246 A | 6/2021 |
| JP | 2022007162 A | 1/2022 |
| WO | 2010119509 A1 | 10/2010 |

OTHER PUBLICATIONS

Dental Access Mobile Clinics (Wayback Machine Screen Capture on Apr. 9, 2019) (Year: 2019).*
Springett, How to Run a Mobile Clinic Off on an Externa Power Source, AVAN Mobility (Sep. 6, 2024) (Year: 2024).*

(Continued)

*Primary Examiner* — Jordan L Jackson
(74) *Attorney, Agent, or Firm* — Dickinson Wright, PLLC

(57) ABSTRACT

A controller of an information processing apparatus is configured to, upon accepting appointments for health checkups from users, present the users with inquiry information inquiring of each user whether to be able to provide a parking place for a vehicle equipped with equipment to be used for the health checkups, and determine a parking place based on replies from the users to an inquiry indicated by the inquiry information.

12 Claims, 4 Drawing Sheets

(56) References Cited

OTHER PUBLICATIONS

Fikar and Hirsch, Home health care routing and scheduling: A review 77 Computer & Operations Research 86-95 (2017) (Year: 2017).*

Mamun et al., Healthcare Monitoring System Inside Self-driving Smart Car in 5G Cellular Network, 2019 IEEE 17th International Conference on Industrial Informatics (INDIN) 1515-1520 (Jan. 30, 2020) (Year: 2020).*

* cited by examiner

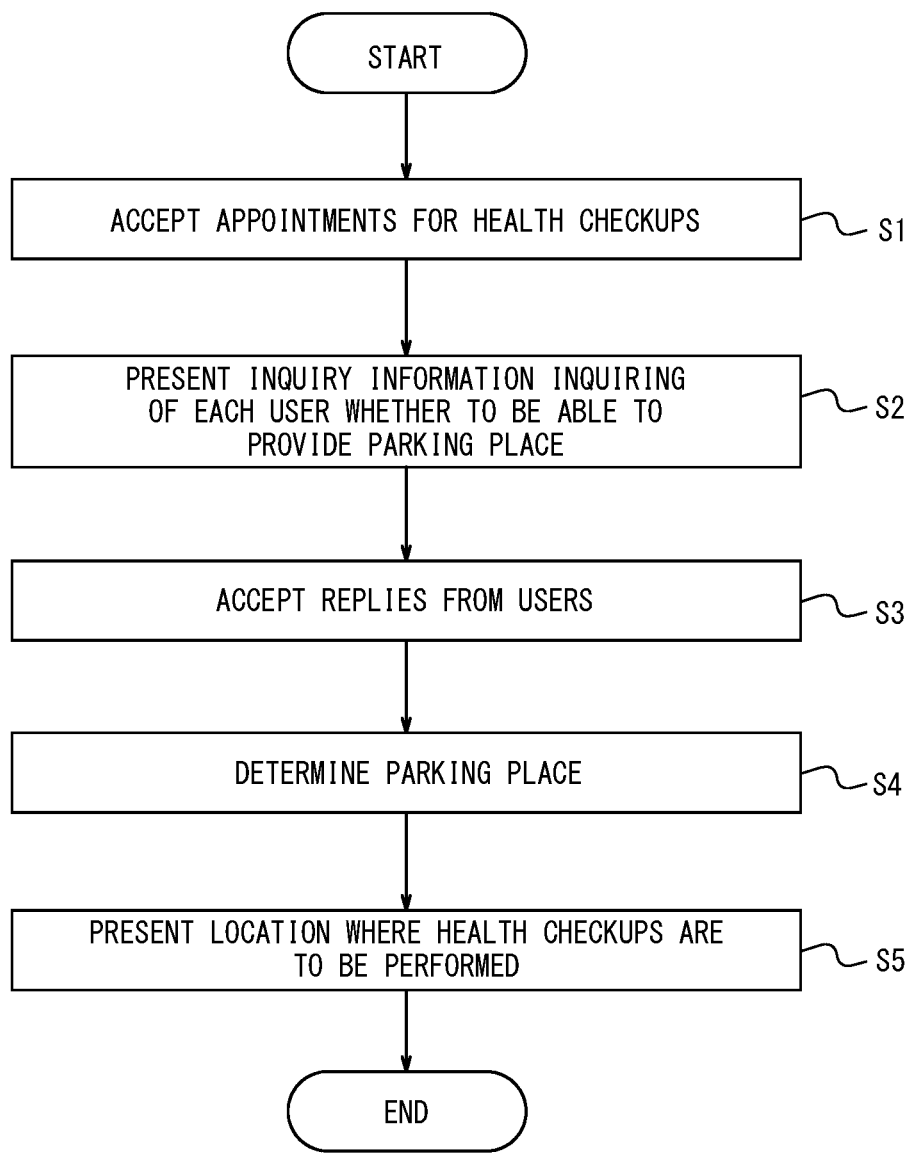

INFORMATION PROCESSING APPARATUS, METHOD, AND NON-TRANSITORY COMPUTER READABLE MEDIUM

CROSS-REFERENCE TO RELATED APPLICATION

This application claims priority to Japanese Patent Application No. 2022-076659, filed on May 6, 2022, the entire contents of which are incorporated herein by reference.

TECHNICAL FIELD

The present disclosure relates to an information processing apparatus, a method, and a program.

BACKGROUND

Patent Literature (PTL) 1 discloses technology for determining health checkup equipment to be installed in a vehicle based on information on users who plan to receive health checkups.

CITATION LIST

Patent Literature

PTL 1: JP 2021-022332 A

SUMMARY

However, the technology is not necessarily convenient because, when receiving health checkups in a vehicle equipped with health checkup equipment, a place for performing the health checkups can be not always allocated in advance. Therefore, there is room for enhancement with respect to technology for improving convenience of health checkups.

It would be helpful to enhance technology for improving convenience of health checkups.

An information processing apparatus according to an embodiment of the present disclosure includes a controller configured to:
upon accepting an appointment for a health checkup from a user, present the user with inquiry information inquiring of the user whether to be able to provide a parking place for a vehicle equipped with equipment to be used for the health checkup; and
determine a parking place based on a reply from the user to an inquiry indicated by the inquiry information.

A method according to an embodiment of the present disclosure is a method performed by an information processing apparatus, the method including:
upon accepting an appointment for a health checkup from a user, presenting the user with inquiry information inquiring of the user whether to be able to provide a parking place for a vehicle equipped with equipment to be used for the health checkup; and
determining a parking place based on a reply from the user to an inquiry indicated by the inquiry information.

A program according to an embodiment of the present disclosure is configured to cause a computer to execute operations, the operations including:
upon accepting an appointment for a health checkup from a user, presenting the user with inquiry information inquiring of the user whether to be able to provide a parking place for a vehicle equipped with equipment to be used for the health checkup; and
determining a parking place based on a reply from the user to an inquiry indicated by the inquiry information.

According to an embodiment of the present disclosure, technology for improving convenience of health checkups can be enhanced.

BRIEF DESCRIPTION OF THE DRAWINGS

In the accompanying drawings:

FIG. 4 is a flowchart illustrating operations of the information processing apparatus according to the embodiment of the present disclosure.

DETAILED DESCRIPTION

Hereinafter, an embodiment of the present disclosure will be described.

Figure 1:
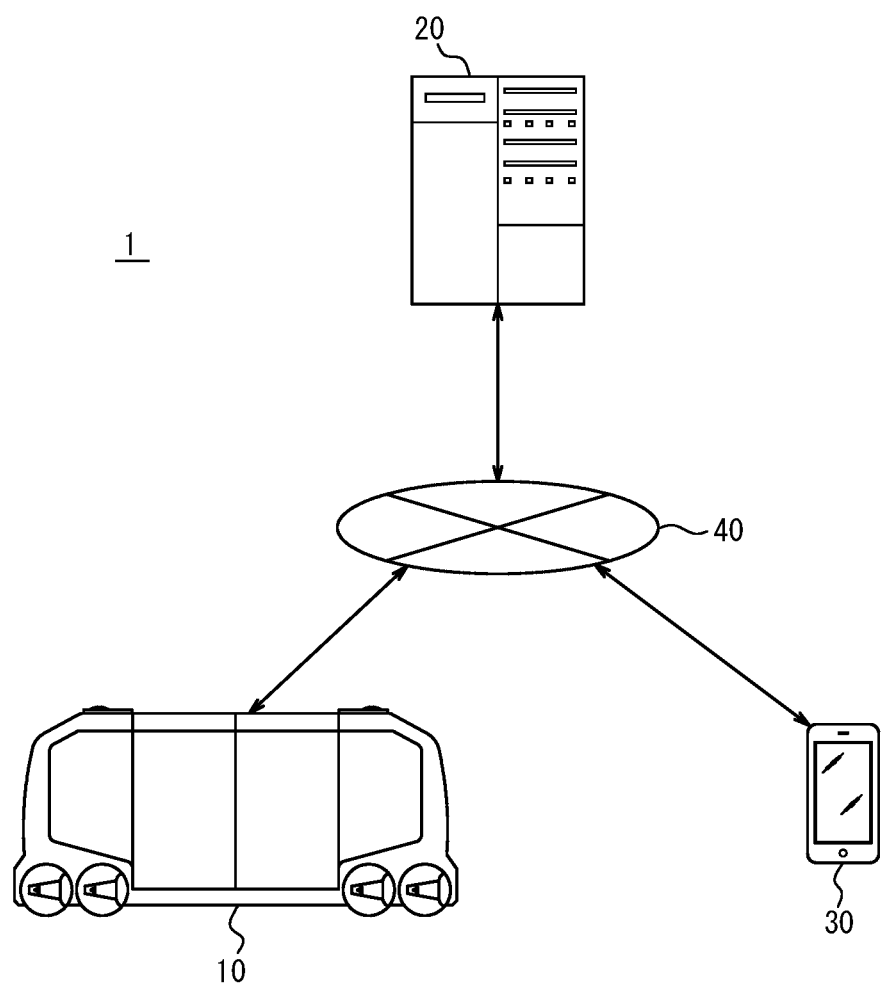
FIG. 1 is a block diagram illustrating a schematic configuration of a system according to an embodiment of the present disclosure.

An outline of a system 1 according to an embodiment of the present disclosure will be described with reference to FIG. 1.

The system 1 includes a vehicle 10, an information processing apparatus 20, and at least one terminal apparatus 30. The vehicle 10, the information processing apparatus 20, and the terminal apparatuses 30 are communicably connected to a network 40.

The vehicle 10 is, for example, an automobile equipped with equipment to be used for health checkups, but not limited to this and may be any vehicle. The automobile is, for example, a gasoline vehicle, a Battery Electric Vehicle (BEV), a Hybrid Electric Vehicle (HEV), a Plug-in Hybrid Electric Vehicle (PHEV), a Fuel Cell Electric Vehicle (FCEV), or the like, but is not limited to these. The vehicle 10 may be driven by a driver, or the driving may be automated at any level. The level of automation is, for example, one of level 1 to level 5 according to the classification of the Society of Automotive Engineers (SAE). The equipment to be used for health checkups may include, for example, a blood pressure monitor, a blood testing apparatus, an electrocardiograph, an X-ray imaging device, an ultrasound apparatus, a computed tomography (CT) apparatus, or a magnetic resonance imaging (MRI) apparatus, but is not limited to these.

The information processing apparatus 20 is a computer such as a server that belongs to a cloud computing system or another type of computing system.

The terminal apparatus 30 is a mobile device such as a mobile phone, a smartphone, or a tablet.

The network 40 includes the Internet, at least one wide area network (WAN), at least one metropolitan area network (MAN), or any combination thereof. The network 40 may include at least one wireless network, at least one optical network, or any combination thereof. The wireless network is, for example, an ad hoc network, a cellular network, a wireless local area network (LAN), a satellite communication network, or a terrestrial microwave network.

An outline of the present embodiment will be described with reference to FIG. 1.

Upon accepting appointments for health checkups from users, a controller 21 of the information processing apparatus 20 presents the users with inquiry information inquiring of each user whether to be able to provide a parking place for the vehicle 10 equipped with equipment to be used for the health checkups. The controller 21 of the information processing apparatus 20 then determines a parking place based on replies from the users to an inquiry indicated by the inquiry information.

According to the present embodiment, the parking place for the vehicle 10 equipped with the equipment to be used for the health checkups, which is to be a location for performing the health checkups, can be allocated in advance. Therefore, technology for improving convenience of health checkups can be enhanced.

Figure 2:
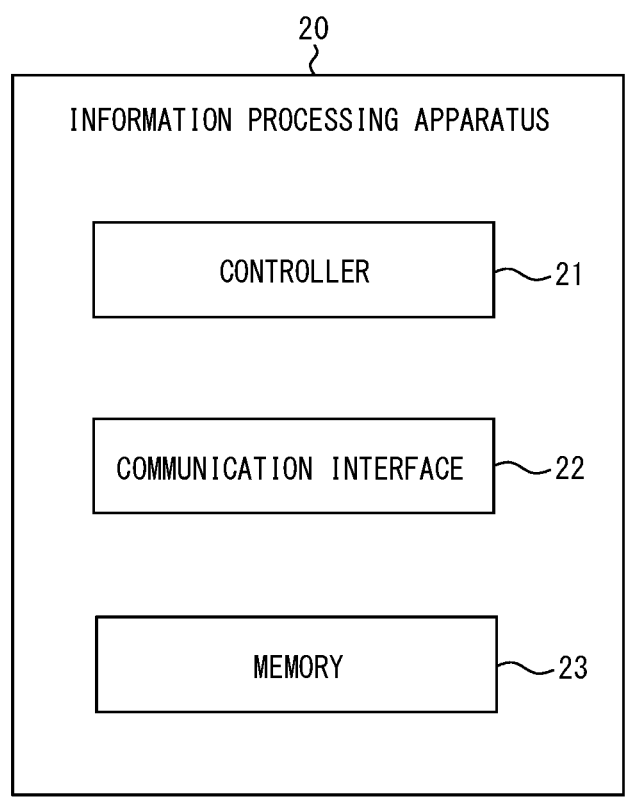
FIG. 2 is a block diagram illustrating a schematic configuration of an information processing apparatus according to the embodiment of the present disclosure.

A configuration of the information processing apparatus 20 according to the present embodiment will be described with reference to FIG. 2.

The information processing apparatus 20 includes the controller 21, a communication interface 22, and a memory 23.

The controller 21 includes at least one processor, at least one programmable circuit, at least one dedicated circuit, or any combination thereof. The processor is a general purpose processor, such as a central processing unit (CPU) or a graphics processing unit (GPU), or a dedicated processor specialized for particular processing. The programmable circuit is, for example, a field-programmable gate array (FPGA). The dedicated circuit is, for example, an application specific integrated circuit (ASIC). The controller 21 executes processes related to operations of the information processing apparatus 20 while controlling components of the information processing apparatus 20.

The communication interface 22 includes at least one interface for communication. The interface for communication is compliant with, for example, a mobile communication standard, a wired LAN standard, or a wireless LAN standard, but not limited to these, and may be compliant with any communication standard. The communication interface 22 receives data to be used for the operations of the information processing apparatus 20, and transmits data obtained by the operations of the information processing apparatus 20.

The memory 23 includes at least one semiconductor memory, at least one magnetic memory, at least one optical memory, or any combination thereof. The semiconductor memory is, for example, random access memory (RAM) or read only memory (ROM). The RAM is, for example, static random access memory (SRAM) or dynamic random access memory (DRAM). The ROM is, for example, electrically erasable programmable read only memory (EEPROM). The memory 23 functions as, for example, a main memory, an auxiliary memory, or a cache memory. The memory 23 stores data to be used for the operations of the information processing apparatus 20 and data obtained by the operations of the information processing apparatus 20. In the present embodiment, the data to be used for the operations of the information processing apparatus 20 includes a system program, an application program, a database, map information, and the like.

Figure 3:
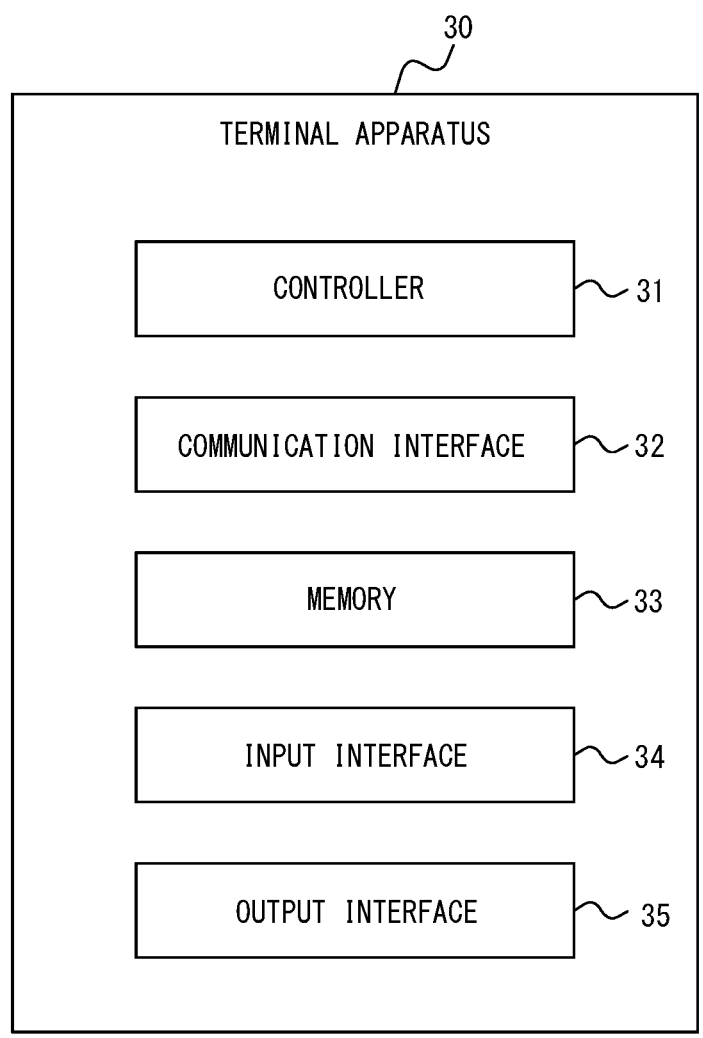
FIG. 3 is a block diagram illustrating a schematic configuration of a terminal apparatus according to the embodiment of the present disclosure.

A configuration of the terminal apparatus 30 according to the present embodiment will be described with reference to FIG. 3.

The terminal apparatus 30 includes a controller 31, a communication interface 32, a memory 33, an input interface 34, and an output interface 35.

The controller 31 includes at least one processor, at least one programmable circuit, at least one dedicated circuit, or any combination thereof. The processor is a general purpose processor such as a CPU or a GPU, or a dedicated processor that is dedicated to specific processing. The programmable circuit is, for example, an FPGA. The dedicated circuit is, for example, an ASIC. The controller 31 executes processes related to operations of the terminal apparatus 30 while controlling components of the terminal apparatus 30.

The communication interface 32 includes at least one interface for communication. The interface for communication is, for example, an interface compliant with a mobile communication standard such as a Long Term Evolution (LTE), the 4th generation (4G) standard, or the 5th generation (5G) standard, an interface compliant with a short-range wireless communication standard such as Bluetooth® (Bluetooth is a registered trademark in Japan, other countries, or both), or a LAN interface. The communication interface 32 receives data to be used for the operations of the terminal apparatus 30, and transmits data obtained by the operations of the terminal apparatus 30.

The memory 33 includes at least one semiconductor memory, at least one magnetic memory, at least one optical memory, or any combination thereof. The semiconductor memory is, for example, RAM or ROM. The RAM is, for example, SRAM or DRAM. The ROM is, for example, EEPROM. The memory 33 functions as, for example, a main memory, an auxiliary memory, or a cache memory. The memory 33 stores data to be used for the operations of the terminal apparatus 30 and data obtained by the operations of the terminal apparatus 30.

The input interface 34 includes at least one interface for input. The interface for input is, for example, a physical key, a capacitive key, a pointing device, a touch screen integrally provided with a display, a camera, a light detection and ranging or laser imaging, detection, and ranging (LiDAR) sensor, or a microphone. The input interface 34 accepts an operation for inputting data to be used for the operations of the terminal apparatus 30. The input interface 34, instead of being included in the terminal apparatus 30, may be connected to the terminal apparatus 30 as an external input device. As an interface for connection, for example, an interface compliant with a standard such as Universal Serial Bus (USB), HDMI® (HDMI is a registered trademark in Japan, other countries, or both), or Bluetooth® can be used.

The output interface 35 includes at least one interface for output. The interface for output is, for example, a display or a speaker. The display is, for example, a liquid crystal display (LCD) or an organic electro luminescent (EL) display. The output interface 35 outputs data obtained by the operations of the terminal apparatus 30. The output interface 35, instead of being included in the terminal apparatus 30, may be connected to the terminal apparatus 30 as an external output device. As an interface for connection, for example, an interface compliant with a standard such as USB, HDMI®, or Bluetooth® can be used.

Operations of the information processing apparatus 20 according to the present embodiment will be described with reference to FIG. 4. These operations correspond to a method according to an embodiment of the present disclosure.

Step S1: The controller 21 of the information processing apparatus 20 accepts appointments for health checkups from users.

Specifically, the controller 31 of each terminal apparatus 30 controls the input interface 34 to accept an operation of each user entering appointment information for a health checkup, on an application running on each terminal apparatus 30 to make appointments for health checkups via the Internet. The controller 31 of each terminal apparatus 30 then controls the communication interface 32 to transmit the appointment information for the health checkup to the information processing apparatus 20. The controller 21 of the information processing apparatus 20 controls the communication interface 22 to receive the appointment information for the health checkup from each terminal apparatus 30. The controller 21 of the information processing apparatus 20 then controls the memory 23 to store the appointment information for the health checkup received from each terminal apparatus 30. The appointment information for the health checkup may include identification information (identification ID or the like) on each terminal apparatus 30 and information on the user (information on name, home location, and the like of the user) who is in possession of each terminal apparatus 30, but is not limited to these.

Step S2: The controller 21 of the information processing apparatus 20 presents the users with inquiry information inquiring of each user whether to be able to provide a parking place for the vehicle 10 equipped with equipment to be used for the health checkups.

Specifically, the controller 21 of the information processing apparatus 20 generates inquiry information (e.g., message) inquiring of each user whether to be able to provide, for example, a parking space in a home of each user, as a parking place for the vehicle 10 equipped with equipment to be used for the health checkups. The controller 21 of the information processing apparatus 20 then controls the communication interface 22 to transmit the inquiry information to each terminal apparatus 30. The controller 31 of each terminal apparatus 30 then controls the communication interface 32 to receive the inquiry information from the information processing apparatus 20. The controller 31 of each terminal apparatus 30 then controls the output interface 35 to output the inquiry information to the user through screen display or audio. The inquiry information may be presented to the user via the application running on the terminal apparatus 30 to make appointments for health checkups via the Internet.

Step S3: The controller 21 of the information processing apparatus 20 accepts replies from the users to an inquiry indicated by the inquiry information of step S2.

Specifically, the controller 31 of each terminal apparatus 30 controls the input interface 34 to accept an operation of the user entering a reply to an inquiry indicated by the inquiry information of step S2. The entry of the reply may be selection of one choice by touch or other means from among multiple choices, displayed on a screen of each terminal apparatus 30, about availability of provision of a parking place. The controller 31 of each terminal apparatus 30 then controls the communication interface 32 to transmit reply information indicating the reply to the information processing apparatus 20. The controller 21 of the information processing apparatus 20 then controls the communication interface 22 to receive the reply information from each terminal apparatus 30.

Step S4: The controller 21 of the information processing apparatus 20 determines, based on the replies of step S3, a parking place for the vehicle 10 equipped with the equipment to be used for the health checkups.

Specifically, the controller 21 of the information processing apparatus 20 identifies, in any method, a reply indicating that a parking place for the vehicle 10 can be provided, from the replies indicated by the reply information received in step S3. The controller 21 of the information processing apparatus 20 then identifies, by referring to the memory 23, a terminal apparatus 30 that has transmitted reply information indicating the identified reply, a user who is in possession of the terminal apparatus 30, and location information on a home of the user. The controller 21 of the information processing apparatus 20 then determines a location indicated by the identified location information on the home, as a parking place for the vehicle 10.

Here, the controller 21 of the information processing apparatus 20 may determine, as a parking place for the vehicle 10, a parking space in a home or the like owned by a user who is able to provide a power supply device to drive the vehicle 10 or the equipment equipped in the vehicle 10 to be used for the health checkups, from among users who have replied that a parking place for the vehicle 10 can be provided. In such a case, as in step S2, the controller 21 of the information processing apparatus 20 can present the users in advance with inquiry information including an inquiry inquiring of each user whether to be able to provide a power supply device to drive the vehicle 10 or the equipment equipped in the vehicle 10 to be used for the health checkups, and, as in step S3, can acquire replies. The power supply device may be a power source for BEVs or PHEVs or a general purpose power source, but is not limited to these.

Step S5: The controller 21 of the information processing apparatus 20 presents, to the users, that the parking place determined in step S4 is a location where the health checkups are to be performed.

Specifically, the controller 21 of the information processing apparatus 20 generates a message informing the users that the parking place determined in step S4 is a location where the health checkups are to be performed. The controller 21 of the information processing apparatus 20 then controls the communication interface 22 to transmit the generated message to each terminal apparatus 30. The controller 31 of each terminal apparatus 30 then controls the communication interface 32 to receive the message. The controller 31 of each terminal apparatus 30 then controls the output interface 35 to output the received message to each user through screen display or audio. This allows each user to know the location of the health checkup.

Subsequently, on a day of the health checkups, the vehicle 10 equipped with the equipment to be used for the health checkups identifies homes of examinees, based on location information on the homes of the examinees of the health checkups acquired from the information processing apparatus 20 via the network 40, picks up the examinees at the homes, and transports the examinees to the location where the health checkups are to be performed (i.e., the parking place determined in step S4). For younger people among the examinees, for example, the health checkups may be performed in the vehicle 10 at the time of pickup.

As described above, upon accepting appointments for health checkups from users, the controller 21 of the information processing apparatus 20 according to the present embodiment presents the users with inquiry information inquiring of each user whether to be able to provide a parking place for the vehicle 10 equipped with equipment to be used for the health checkups. The controller 21 of the information processing apparatus 20 then determines a parking place based on replies from the users to an inquiry indicated by the inquiry information.

According to such a configuration, the parking place for the vehicle 10 equipped with the equipment to be used for the health checkups, which is a location where the health checkups are to be performed, can be allocated in advance. Therefore, technology for improving convenience of health checkups can be enhanced.

While the present disclosure has been described with reference to the drawings and examples, it should be noted that various modifications and revisions may be implemented by those skilled in the art based on the present disclosure. Accordingly, such modifications and revisions are included within the scope of the present disclosure. For example, functions or the like included in each component, each step, or the like can be rearranged without logical inconsistency, and a plurality of components, steps, or the like can be combined into one or divided.

As a variation, an embodiment in which the configuration and operations of the information processing apparatus 20 are distributed to multiple computers capable of communicating with each other can be implemented. For example, an embodiment in which some or all of the components of the information processing apparatus 20 are provided in the vehicle 10 can also be implemented.

As a variation, the controller 21 of the information processing apparatus 20 may determine to give an incentive to the user, among the users, who has provided the parking place determined in step S4 in the embodiment described above. The incentive may include a lower fee for a health checkup or increased items for a health checkup, but is not limited to these.

As a variation, an embodiment in which a general purpose computer functions as the information processing apparatus 20 according to the above embodiment can also be implemented. Specifically, a program in which processes for realizing the functions of the information processing apparatus 20 according to the above embodiment are written may be stored in a memory of a general purpose computer, and the program may be read and executed by a processor. Accordingly, the present disclosure can also be implemented as a program executable by a processor, or a non-transitory computer readable medium storing the program.

A part of the present embodiment will be exemplarily described below. However, it should be noted that the embodiment of the present disclosure is not limited to these.

[Appendix 1] An information processing apparatus comprising a controller configured to:
upon accepting an appointment for a health checkup from a user, present the user with inquiry information inquiring of the user whether to be able to provide a parking place for a vehicle equipped with equipment to be used for the health checkup; and
determine a parking place based on a reply from the user to an inquiry indicated by the inquiry information.

[Appendix 2] The information processing apparatus according to Appendix 1, wherein the inquiry information includes an inquiry as to whether the user is able to provide a power supply device to drive the vehicle or the equipment.

[Appendix 3] The information processing apparatus according to Appendix 1 or 2, wherein the controller is configured to determine to give an incentive to a user who has provided the parking place.

[Appendix 4] The information processing apparatus according to any one of Appendices 1 to 3, wherein the parking place includes a parking space in a home of the user.

[Appendix 5] The information processing apparatus according to any one of Appendices 1 to 4, wherein the health checkup is performed in the vehicle parked in the parking place.

[Appendix 6] A method performed by an information processing apparatus, the method comprising:
upon accepting an appointment for a health checkup from a user, presenting the user with inquiry information inquiring of the user whether to be able to provide a parking place for a vehicle equipped with equipment to be used for the health checkup; and
determining a parking place based on a reply from the user to an inquiry indicated by the inquiry information.

[Appendix 7] The method according to Appendix 6, wherein the inquiry information includes an inquiry as to whether the user is able to provide a power supply device to drive the vehicle or the equipment.

[Appendix 8] The method according to Appendix 6 or 7, further comprising determining to give an incentive to a user who has provided the parking place.

[Appendix 9] The method according to any one of Appendices 6 to 8, wherein the parking place includes a parking space in a home of the user.

[Appendix 10] The method according to any one of Appendices 6 to 9, wherein the health checkup is performed in the vehicle parked in the parking place.

[Appendix 11] A program configured to cause a computer to execute operations, the operations comprising:
upon accepting an appointment for a health checkup from a user, presenting the user with inquiry information inquiring of the user whether to be able to provide a parking place for a vehicle equipped with equipment to be used for the health checkup; and
determining a parking place based on a reply from the user to an inquiry indicated by the inquiry information.

[Appendix 12] The program according to Appendix 11, wherein the inquiry information includes an inquiry as to whether the user is able to provide a power supply device to drive the vehicle or the equipment.

[Appendix 13] The program according to Appendix 11 or 12, wherein the operations further comprise determining to give an incentive to a user who has provided the parking place.

[Appendix 14] The program according to any one of Appendices 11 to 13, wherein the parking place includes a parking space in a home of the user.

[Appendix 15] The program according to any one of Appendices 11 to 14, wherein the health checkup is performed in the vehicle parked in the parking place.

The invention claimed is:

1. A system comprising an autonomous vehicle comprising equipment to be used for a health checkup, an information processing apparatus and a terminal apparatus, wherein the information processing apparatus comprises a controller configured to:
upon accepting an appointment for a health checkup from a user, present the user with inquiry information inquiring of the user whether the user is able to provide a parking place for the autonomous vehicle equipped with equipment to be used for the health checkup, by sending the inquiry information to the terminal apparatus;
receive, from the terminal apparatus, reply information that indicates a reply from the user to an inquiry indicated by the inquiry information, and
determine a parking place based on the reply;
wherein the inquiry information includes an inquiry as to whether the user is able to provide a power supply device to drive the equipment including at least one of a blood pressure monitor, a blood testing apparatus, an electrocardiogram X-ray imaging device, an ultrasound apparatus, a computed tomography (CT) apparatus, and a magnetic resonance imaging (MRI) apparatus;

the terminal apparatus comprises a controller configured to:

output the inquiry information, accept the reply to the inquiry from the user, and send the reply information to the information processing apparatus;

wherein the information processing apparatus controls the autonomous vehicle to travel autonomously to the determined parking place based on the reply information.

2. The information processing apparatus according to claim 1, wherein the controller is configured to determine to give an incentive to a user who has provided the parking place.

3. The information processing apparatus according to claim 1, wherein the parking place includes a parking space in a home of the user.

4. The information processing apparatus according to claim 1, wherein the health checkup is performed in the vehicle parked in the parking place.

5. A method performed by a system comprising an autonomous vehicle comprising equipment to be used for a health checkup, an information processing apparatus, and a terminal apparatus, the method comprising:

upon accepting an appointment for a health checkup from a user, presenting the user with inquiry information inquiring of the user whether the user is able to provide a parking place for the autonomous vehicle equipped with equipment to be used for the health checkup, by sending the inquiry information to the terminal apparatus;

receiving, from the terminal apparatus, reply information that indicates a reply from the user to an inquiry indicated by the inquiry information; and determining a parking place based on the reply;

wherein the inquiry information includes an inquiry as to whether the user is able to provide a power supply device to drive the equipment including at least one of a blood pressure monitor, a blood testing apparatus, an electrocardiogram X-ray imaging device, an ultrasound apparatus, a computed tomography (CT) apparatus, and a magnetic resonance imaging (MRI) apparatus;

the method further comprises outputting the inquiry information, accepting the reply to the inquiry from the user, and sending the reply information to the information processing apparatus;

wherein the method further comprises controlling the autonomous vehicle to travel autonomously to the determined parking place based on the reply information.

6. The method according to claim 5, further comprising determining to give an incentive to a user who has provided the parking place.

7. The method according to claim 5, wherein the parking place includes a parking space in a home of the user.

8. The method according to claim 5, wherein the health checkup is performed in the vehicle parked in the parking place.

9. A non-transitory computer readable medium storing a program configured to cause a computer to execute operations, the operations comprising:

upon accepting an appointment for a health checkup from a user, presenting the user with inquiry information inquiring of the user whether the user is able to provide a parking place for an autonomous vehicle equipped with equipment to be used for the health checkup, by sending the inquiry information to a terminal apparatus;

receiving, from the terminal apparatus, reply information that indicates a reply from the user to an inquiry indicated by the inquiry information; and determining a parking place based on the reply;

wherein the inquiry information includes an inquiry as to whether the user is able to provide a power supply device to drive the equipment including at least one of a blood pressure monitor, a blood testing apparatus, an electrocardiogram X-ray imaging device, an ultrasound apparatus, a computed tomography (CT) apparatus, and a magnetic resonance imaging (MRI) apparatus;

the operations further comprising outputting the inquiry information, accepting the reply to the inquiry from the user, and sending the reply information to the information processing apparatus;

wherein the operations further comprise controlling the autonomous vehicle to travel autonomously to the determined parking place based on the reply information.

10. The non-transitory computer readable medium according to claim 9, wherein the operations further comprise determining to give an incentive to a user who has provided the parking place.

11. The non-transitory computer readable medium according to claim 9, wherein the parking place includes a parking space in a home of the user.

12. The non-transitory computer readable medium according to claim 9, wherein the health checkup is performed in the vehicle parked in the parking place.

* * * * *